United States Patent [19]

Fox et al.

[11] Patent Number: 4,963,364

[45] Date of Patent: Oct. 16, 1990

[54] MICROENCAPSULATED ANTITUMOR AGENT

[76] Inventors: Sidney W. Fox, 12500 SW. 152 St., Bldg. B, Rm 115, Miami, Fla. 33177; Robert W. Veltri, 7658 Standish Pl., Suite 107, Rockville, Md. 20855

[21] Appl. No.: 335,952

[22] Filed: Apr. 10, 1989

[51] Int. Cl.$^5$ .............................................. A61K 9/66
[52] U.S. Cl. .................................... 424/455; 424/484; 424/491
[58] Field of Search ..................... 424/491, 455, 484; 514/885, 974

[56] References Cited

U.S. PATENT DOCUMENTS

| | | | |
|---|---|---|---|
| 3,052,655 | 9/1962 | Fox et al. | 528/313 |
| 3,076,790 | 2/1963 | Fox et al. | 528/313 |
| 4,774,320 | 9/1988 | Tagliabue et al. | 514/885 X |
| 4,832,686 | 5/1989 | Anderson | 514/885 X |
| 4,844,904 | 7/1989 | Hamaguchi et al. | 514/885 X |
| 4,873,088 | 10/1989 | Mayhew et al. | 514/974 X |
| 4,877,611 | 10/1989 | Cantrell | 514/885 X |

Primary Examiner—Thurman K. Page
Attorney, Agent, or Firm—Peter R. Bahn

[57] ABSTRACT

Thermally polymerized copolyamino acids are used to microencapsulate a chemotherapeutic compound for more efficient drug delivery.

1 Claim, 2 Drawing Sheets

COMPARISON OF ADRIAMYCIN AND RS VII 48 VD ENCAPSULATED ADRIAMYCIN ON SURVIVAL OF MICE BEARING L1210 LEUKEMIA (60 DAY DATA)

Numbers on Bars = Survivors

ILS = Increased Life Span

Adriamycin Alone

RS VII 48 VD Encapsulated Adriamycin

COMPARISON OF ADRIAMYCIN AND RS VII 48 VD ENCAPSULATED ADRIAMYCIN ON SURVIVAL OF MICE BEARING L1210 LEUKEMIA
(30 DAY DATA)

Numbers on Bars = Survivors

ILS = Increased Life Span

Adriamycin Alone

RS VII 48 VD Encapsulated Adriamycin

COMPARISON OF ADRIAMYCIN AND RS VII 48 VD ENCAPSULATED ADRIAMYCIN ON SURVIVAL OF MICE BEARING L1210 LEUKEMIA
(60 DAY DATA)

Numbers on Bars = Survivors

ILS = Increased Life Span

Adriamycin Alone

RS VII 48 VD Encapsulated Adriamycin

MICROENCAPSULATED ANTITUMOR AGENT

REFERENCE CITED

U.S. Patent Documents

U.S. Pat. No. 3,052,655, 9/1962, Fox et al, 528/313.
U.S. Pat. No. 3,076,790, 2/1963, Fox et al, 528/313.

Other Publications

Fox et al., *Science*, 128:124 (1958)
Fox, *Science*, 132:200 (1960)

FIELD OF THE INVENTION

This invention relates to the fields of protein engineering, microencapsulation, and pharmacology in general. It also relates to the fields of thermally engineered proteins and antitumor chemotherapeutics in particular.

BACKGROUND OF THE INVENTION

Among those chemotherapeutic compounds known to possess antitumor activity in mammalian systems is adriamycin, which has the molecular structure shown below.

The pharmacological effectiveness of many drugs is greatly enhanced when they are released continuously over an extended time in subject animals in contrast to when the same drugs are administered all at once or in several discrete doses.

One of the methods by which drugs may be slowly released in subject animals is to microencapsulate the drugs within suitable biocompatible vehicles that allow drugs to slowly leak through the vehicle boundaries.

Lipid vesicles, or liposomes, have been found to be one type of drug delivery vehicle which can be used to microencapsulate various chemotherapeutics. However, liposomes suffer from the following defects. The timed released fo chemotherapeutics through lipid vesicle membranes are often difficult to control and to vary in an easily selectable manner. Some of the lipids employed in liposome drug carriers are difficult to synthesize and therefore expensive. Liposomes also have limited stability and considerable nonuniformity. Many types of lipids are not well tolerated by mammals.

In contrast to the use of lipids as the main constituent of drug delivery vehicles, polyamino acids offer several potential advantages. Polyamino acids are inexpensive, readily available in large quantities, and are readily compatible with biological systems.

It was discovered previously that thermal peptides and proteins can be made simply by heating amino acids together in a flask for several hours (Fox et al., 1958). Such compounds and methods for their preparation are described in U.S. Pat. Nos. 3,052,655 and 3,076,790, by Fox et al.

Thermal copolyamino acids form a class of thermally engineered proteins because they possess amino acid sequence that have not been currently found in nature. They sometimes are referred to as proteinoids to reflect the fact that, although they resemble proteins structurally and functionally, they are produced abiotically in contrast to biologically generated proteins such as hemoglobin, to use just one example. They are also referred to as thermal proteins for the same reason. Organisms do not make protein by heating amino acids.

Thermally engineered proteins, or proteinoids, are much easier to manufacture than proteins which are engineered by genetic means or by standard organic synthetic means.

It was previously found that thermal copolyamino acids, upon being heated in aqueous solution and allowed to cool, spontaneously form microspheres or microcapsules approximately one micron in size (Fox, 1960).

The object of this invention was to employ thermal copolyamino acids as a vehicle for the microencapsulation and in vivo delivery of a chemotherapeutic compound.

SUMMARY OF THE INVENTION

A microencapsulated antitumor agent was prepared by heat-polymerizing amino acids and forming microspheres from the resulting polymer while trapping adriamycin within the microspheres.

Thermal copolyamino acid microspheres containing adriamycin demonstrate an enhanced ability to prolong the lives of leukemic mice when compared to adriamycin alone.

DETAILED DESCRIPTION OF THE INVENTION

Preparation of Thermal Copolyamino Acid RS VII 48 VD

Thermal copolyamino acid RS VII 48 VD was prepared by mixing 3.325 grams of L-aspartic acid, 7.35 grams of L-glutamic acid, and 15.50 grams of L-histidine (i.e. molar ratios of Asp:Glu:His 1:2:4) together with 25 ml of distilled water in a flask. The flask was heated under nitrogen at 200° C. for 24 hours. After being allowed to cool, the resulting glassy substance was mixed with 250 ml of distilled water to form a slurry. The alurry was transferred to dialysis tubing with a molecular weight cut-off of approximately 6000 Daltons and the material dialyzed for 3 days against distilled water. The dialysate was then filtered through Whatman No. 1 filter paper. The fraction retained by the filter paper was then dried in a desiccator, and used as described below.

Thermal Copolyamino Acid Microencapsulation of Adriamycin

Micorencapsulation was accomplished by mixing 25 mg of thermal copolyamino acid RS VII 48 VD with 1.0 ml of distilled water in a test tube and heating until the polymer dissolved. Then 1.0 ml of heated distilled water containing 10 mg of adriamycin was added to the test tube containing the polymer. Upon being allowed to cool, the liquid became cloudy as polymer microcapsules spontaneously formed, trapping adriamycin within their interiors. Free adriamycin was removed by washing the adriamycin-containing microcapsules several times in 1% sodium chloride solution. The entrapment may take place within a matrix as well as within microcapsules. As in the case of lipid vesicles thermal copolyamino acid microcapsules can also be made by sonication.

In Vivo Test of Microencapsulated Adriamycin

Figure 1:
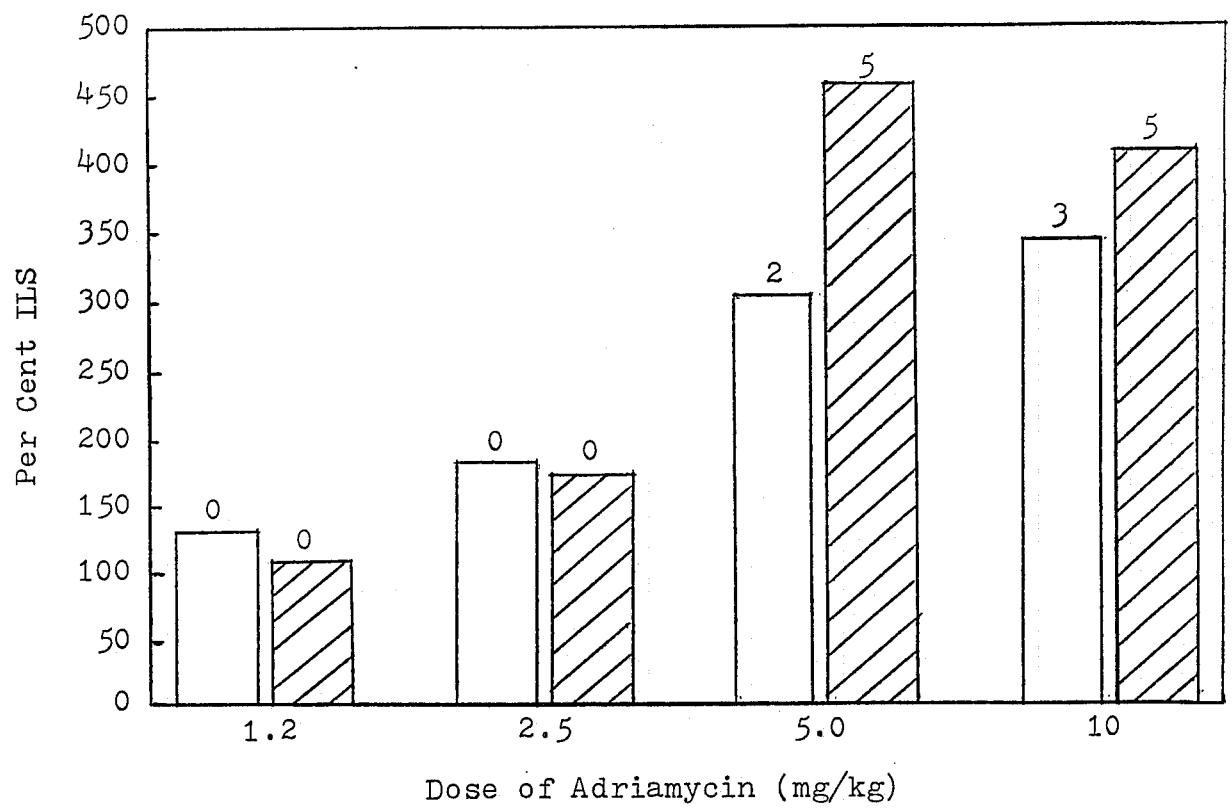
FIG. 1 shows a comparison of adriamycin and thermal copolyamino acid RS VII 48 VD encapsulated adriamycin on the survival of mice bearing L1210 leukemia (30 day data).
Figure 1:
Figure 1:
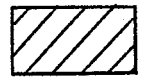
Figure 2:
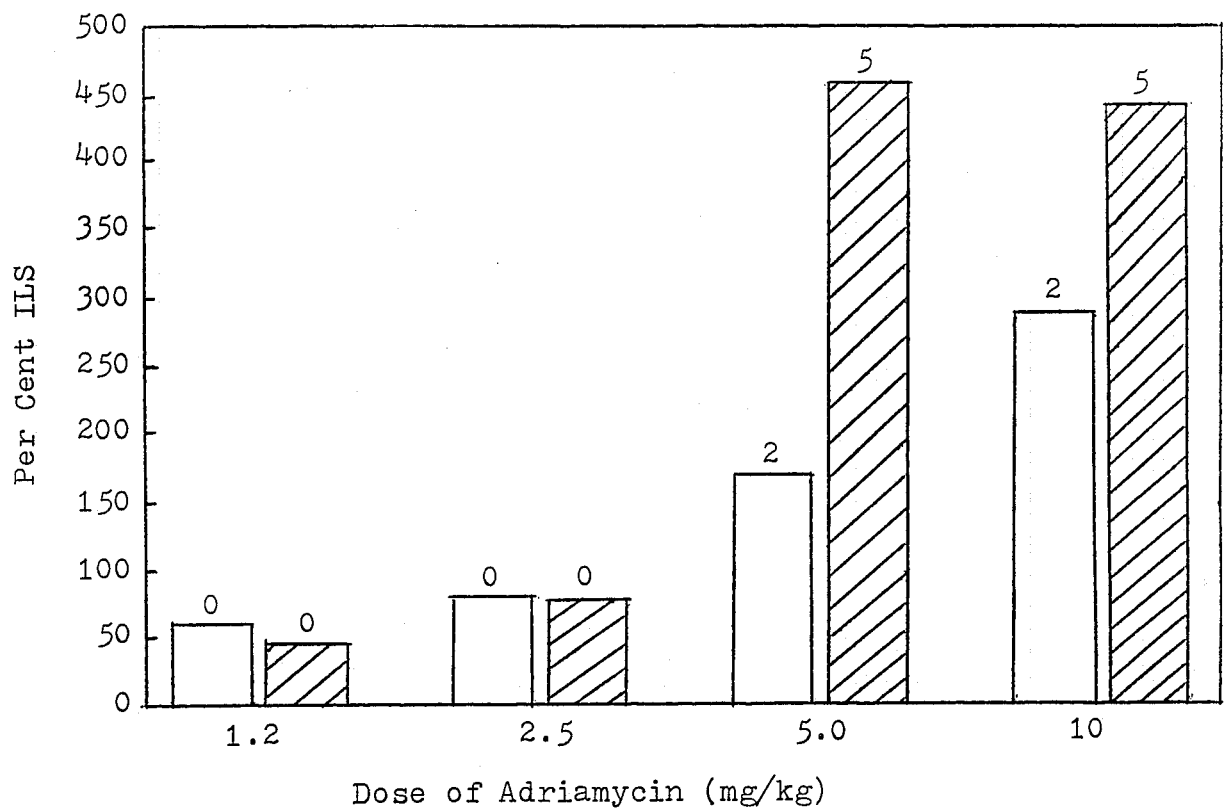
FIG. 2 shows a comparison of adriamycin and thermal copolyamino acid RS VII 48 VD encapsulated adriamycin on the survival of mice bearing L1210 leukamia (60 day data).
Figure 2:
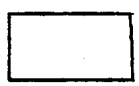
Figure 2:
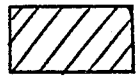

Mice, in groups of twelve, were innoculated on Day 0 with $10^5$ L1210 murine leukemia cells. They were then treated, starting one day later, with either adriamycin alone, microencapsulated adriamycin, or thermal copolyamino acid microcapsules alone. The animals received injections of the test compounds on Days 1, 5, 9 according to established National Cancer Institute protocols. Survival of the mice was scored at 30 day (Table 1 and FIG. 1). and at 60 days (Table 2 and FIG. 2).

Experimental Results

At 30 days, there was significant improvement in Increased Life Span (ILS) for groups of mice receiving 10 and 5 mg/kg of microencapsulated adriamycin (178.9% and 200.1% respectively) over those animals receiving adriamycin alone (147.9% and 130.6% respectively). When scoring for survivors, 10 out of 12 animals in these two microencapsulated adriamycin groups were still alive compared to 5 out of 12 animals in the adriamycin only groups.

The 10 survivors from the microencapsulation protocol persisted and were still alive at 60 days. This represents greater than 80% survival at these treatment doses. With adriamycin only, one other animal had died by 60 days, leaving 4 survivors for an overall 33% survival in these two groups. These results are reflected in the ILS values where the microencapsulated adriamycin groups concluded the experiment with a remarkable 450% Increased Life Span.

TABLE 1

EFFECT OF RS VII 48 VD ENCAPSULATED ADRIAMYCIN ON L1210 LEUKEMIA IN VIVO AS MEASURED AT 30 DAYS

| Test Sample | Conc. mg/kg | Mean Survival at Day 30 (Days) | ILS % | Survivors at Day 30 |
|---|---|---|---|---|
| RS VII 48 VD/ Adriamycin | 10 | 28.3 | 178.9 | 5 |
|  | 5.0 | 29.5 | 200.1 | 5 |
|  | 2.5 | 17.3 | 76.5 | 0 |
|  | 1.2 | 14.5 | 47.9 | 0 |
| Adriamycin Only | 10 | 24.3 | 147.9 | 3 |
|  | 5.0 | 22.6 | 130.6 | 2 |
|  | 2.5 | 17.6 | 79.7 | 0 |
|  | 1.2 | 15.5 | 57.7 | 0 |
| RS VII 48 VD Only | 10 eq | 11.2 | 13.6 | 0 |
|  | 5.0 eq | 10.7 | 8.5 | 0 |
|  | 2.5 eq | 10.7 | 8.5 | 0 |
|  | 1.2 eq | 10.2 | 3.4 | 0 |

ILS = Increased Life Span

TABLE 2

EFFECT OF RS VII 48 VD ENCAPSULATED ADRIAMYCIN ON L1210 LEUKEMIA IN VIVO AS MEASURED AT 60 DAYS

| Test Sample | Conc. mg/kg | Mean Survival at Day 60 (Days) | ILS % | Survivors at Day 60 |
|---|---|---|---|---|
| RS VII 48 VD/ Adriamycin | 10 | 53.3 | 442.2 | 5 |
|  | 5.0 | 54.5 | 454.0 | 5 |
|  | 2.5 | 17.3 | 76.5 | 0 |
|  | 1.2 | 14.5 | 47.9 | 0 |
| Adriamycin Only | 10 | 37.5 | 281.5 | 2 |
|  | 5.0 | 26.5 | 169.5 | 2 |
|  | 2.5 | 17.6 | 79.7 | 0 |
|  | 1.2 | 15.5 | 57.7 | 0 |
| RS VII 48 VD Only | 10 eq | 11.2 | 13.6 | 0 |
|  | 5.0 eq | 10.7 | 8.5 | 0 |
|  | 2.5 eq | 10.7 | 8.5 | 0 |
|  | 1.2 eq | 10.2 | 3.4 | 0 |

ILS = Increased Life Span

What is claimed is:

1. A microencapsulated drug delivery vehicle comprising the drug adriamycin enclosed within a thermal copolyamino acid microsphere wherein the said copolyamino acid was polymerized from a mixture of aspartic acid, glutamic acid, and histidine in a ratio of 1:2:4.